US00PP29958P3

(12) United States Plant Patent
Austin

(10) Patent No.: US PP29,958 P3
(45) Date of Patent: Dec. 11, 2018

(54) ***ROSA HYBRIDA* SHRUB NAMED 'AUSAPPLY'**

(50) Latin Name: *Rosa hybrida*
Varietal Denomination: AUSapply

(71) Applicant: David Austin Roses Ltd., Albrighton, Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 2 days.

(21) Appl. No.: 15/731,223

(22) Filed: May 4, 2017

(65) Prior Publication Data

US 2018/0092266 P1 Mar. 29, 2018

(30) Foreign Application Priority Data

Sep. 29, 2016 (QZ) ..... PBR 2016/2374

(51) Int. Cl.
*A01H 5/02* (2018.01)
*A01H 6/74* (2018.01)

(52) U.S. Cl.
USPC ..... Plt./107
CPC ..... *A01H 5/02* (2013.01); *A01H 6/749* (2018.05)

(58) Field of Classification Search
USPC ..... Plt./101, 102, 107
See application file for complete search history.

*Primary Examiner* — Susan McCormick Ewoldt
*Assistant Examiner* — Karen M Redden
(74) *Attorney, Agent, or Firm* — KPPB LLP

(57) ABSTRACT

A variety of rose plant of the shrub class, named 'AUSapply'. The 'AUSapply' is a variety of a rose suitable for cut-flower production with large flowers having around 100 petals, having an intense deep pink color, and a strong fruity fragrance.

1 Drawing Sheet

Classification: The present invention relates to a new *Rosa hybrida* shrub of the market class 'English Rose'.

Variety denomination: The new plant has the varietal denomination 'AUSapply'.

CROSS-REFERENCE TO RELATED APPLICATION

The present application claims priority to European CPVO 2016/2374, filed Sep. 29, 2016.

ORIGIN OF INVENTION

This invention relates to a new and distinct variety of shrub rose plant named 'AUSapply', which was originated from the cross-pollination of the two 'unnamed' and unpatented seedlings of *Rosa hybrida.*

BACKGROUND OF THE INVENTION

The primary objective of this breeding was to produce a rose variety suitable for cut-flower production with large flowers having around 100 petals and having an intense deep pink color.

SUMMARY OF THE INVENTION

Among the features which distinguish the new variety from others presently available and commercial rose cultivars known to the inventor is the following combination of characteristics: large blooms with around 100 petals and an even and intense shade of deep pink coloring.

Asexual reproduction of the new variety by budding as performed at Bowling Green Lane in Albrighton, Britain shows that the foregoing and other distinguishing characteristics come true to form and are established and transmitted through succeeding asexual propagations. 'AUSapply' may be asexually propagated by budding. The budding successfully occurred on the plant/rootstock *Rosa Inermis* for the observed plants.

COMPARISON WITH PARENTS

The maternal and paternal parents of 'AUSapply' are two unnamed seedlings. The new rose may be distinguished from its maternal parent, by the following combination of characteristics: the maternal parent is of a paler pink color with a smaller, more cupped bloom. The new rose may be distinguished from its pollen parent, by the following combination of characteristics: the paternal parent has a Hybrid Tea bloom formed of a brighter pink and no fragrance.

COMPARISON WITH THE CLOSEST COMMERCIALLY AVAILABLE CULTIVAR

The closest commercially available cultivars to the new variety are the 'AUSchris' (U.S. Plant Pat. No. 24,462). The new rose may be distinguished from the 'AUSchris' based on the number of petals, which are far fewer in number (~65 petals). It may also be distinguished by the fact that the 'AUSchris' bloom has a darker pink and the petals are of a uniform color on both sides, whereas the petals of 'AUSapply' are slightly paler on the reverse. Finally, the base petals of 'AUSchris' have a yellow spot, whereas the 'AUSapply' has a white spot.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

Observations of budded 'AUSapply' specimens were made at the nursery at David Austin Roses Limited in Albrighton, Wolverhampton, United Kingdom. The following description is of 5 year-old rose plants of the new variety grown in a garden environment in Albrighton, Britain in the month of May. Phenotypic expression may vary with environmental, cultural and climatic conditions, as well as differences in conditions of light and soil.

Flower characteristics:

*Blooming habit.*—Continuous. The number of blooms per plant during the growing season is profuse, but there are too many to count.

*Bud.*—Size: About 2.8 cm long and 2.8 cm in diameter when the petals start to unfurl. Form: The bud form is pointed globular. Color: When sepals first divide, the bud color is RHS 59A (red-purple group). When half blown, the upper sides of the petals are RHS 61C (red-purple group), and the lower sides of the petals RHS 62B (red-purple group). Calyx: Shape: opens to a star shape, with the sepals finally folding back against the stems. Length: 8-8.5 cm. Diameter: 8-8.5 cm. Sepals: Arrangement: Regularly arranged. Color: Upper Surface: RHS 144A (yellow-green group). Lower Surface: RHS 144A (yellow-green group). Length: 3.5 cm. Width: 9-11 mm. Shape: Lanceolate. Surface texture: Upper Surface: Slightly Downy. Lower Surface: Smooth. Number: There are 3 lightly appendaged sepals, and 2 unappendaged sepals with hairy edges. Receptacles: Color: RHS 143C (green group). Shape: Funnel. Size: Medium, about 1 cm long×1 cm wide. Surface: Smooth. Peduncle: Length: Short, averaging about 11 cm. Surface: Prickly. Color: RHS 143C (green group) dappled with RHS 183B (greyed-purple group). Strength: Normal.

*Blooms.*—Size: Very large, average open diameter is about 11 cm. Borne: Mostly singly in clusters of between 1 to 4 and having a rounded shape. Stems: Strength: Normal, average length is about 85 cm. Diameter: 6 mm. Form: When first open, bloom is cupped. Permanence of bloom: outer petals curl back.

*Petalage.*—Number of petals under normal conditions: 100. Color: The upper sides of the petals are RHS N66B (red-purple group). The reverse sides of the petals are RHS N66D (red-purple group). The base of the petals has a spot that is RHS N155A (white group). Variegations: None. Discoloration: The general tonality at the end of the first day is RHS N66A (red-purple group), and at the end of the third day is RHS N66B (red-purple group). Fragrance: Strong. Character of fragrance: Fruity.

*Petals.*—Texture: Velvety. Size: Width: 3.5 cm. Length: 6 cm. Surface: Smooth. Shape: Obovate. Margin: Medium reflexing with weak incisions. Apex Shape: Rounded. Base Shape: Acuminate. Form: Slightly incurved, with some petals folded. Arrangement: Regularly arranged. Petaloids: Number: Around 8-10. Color: RHS N166B (red-purple group). Length: between 8-25 mm. Width: between 7-18 mm. Shape: Obovate. Margin: Uniform. Persistence: Petals hang on and dry. Lastingness: On the plant: not tested. As a cut flower: long about 10 days.

*Reproductive parts.*—Stamens: Number: between 4-10. Length: 1 cm. Anthers: Length: 2 mm. Color: RHS N155A (white group). Arrangement: Mixed with petaloids. Filaments: Color: RHS N155A (white group). Length: 7 mm. Pollen: Color: RHS 21B (yellow-orange group). Amount: Scarce. Pistils: Number: 30. Length: between 9-12 mm. Styles: Color: RHS N155A (white group). Length: between 7-10 mm. Stigmas: Color: RHS 1C (green-yellow group). Length: 1 mm. Hips: NONE Observed.

Plant characteristics:

*Plant form.*—Shrub.

*Plant growth.*—Vigorous and semi-upright.

*Age to maturity.*—2 years.

*Mature plant.*—Height: 1 m 10 cm. Width: 50 cm.

*Rootstock.*—*Rosa Inermis* for the observed plants.

*Foliage.*—Number: Leaflets on normal mid-stem leaves is: 5 mostly (some 3)(including terminal leaflet). Size: Large, about 19 cm long×15 cm wide. Quantity: Normal. Number of leaves per flowering stem is: 10. Color: New foliage: Upper side: RHS 144A (yellow-green group). Lower side: RHS 146D (yellow-green group) with RHS 61A (red-purple group) veins. Old foliage: Upper side: RHS 147A (yellow-green group). Lower side: RHS 147B (yellow-green group).

*Leaflets.*—Size: About 7 cm long×5 cm wide. Shape: Ovate. Base Shape: Rounded. Apex Shape: Acuminate. Texture: Leathery. Edge: Serrated. Serrations: Single. Petiole: Color: RHS 146A (yellow-green group). Length: 5 cm. Width: 2 mm. Surface Texture: Glandular. Petiole Rachis: Color: RHS 146A (yellow-green group). Underside: glandular with prickles. Stipules: Length: 3 cm, glandular. Color: RHS 146A (yellow-green group). Auricle: Shape: Lanceolate. Length: 12 mm. Width: 2.5 mm. Color: RHS 146A (yellow-green group). Vein Color: Color: Same as leaf color. Venation Pattern: Reticulate.

*Wood.*—New Wood: Color: RHS 144A (yellow-green group). Bark: Smooth. Old Wood: Color: RHS 144A (green group) with some RHS 182A (greyed-red group). Bark: Rough.

*Branching habit.*—Number: None-all stems come from base with a flower cluster at the top.

*Stems.*—Mature Stem: Length: 85 cm. Diameter: 6 mm. Internode Distance: 9 cm. The above measurements are all variable, depending on growing conditions in a season. Stem Pubescence Present: No.

*Prickles.*—Quantity: On main canes from base: None.

*Small prickles.*—Quantity: Main stalk: Few. Number per stem length: 2-3 per 20 cm. Laterals: No laterals. Color: When young: RHS 178B (greyed-red color). When mature: RHS 178B (greyed-red color).

*Disease resistance.*—Powdery Mildew: Resistant. Downy Mildew: Resistant. Blackspot: Resistant. Rust: Resistant.

*Pest resistance.*—Not tested.

*Winter hardiness.*—Not tested.

*Growing conditions.*—Normal garden conditions.

What is claimed is:

1. A new and distinct variety of rose plant of the shrub class, substantially as herein shown and described.

* * * * *

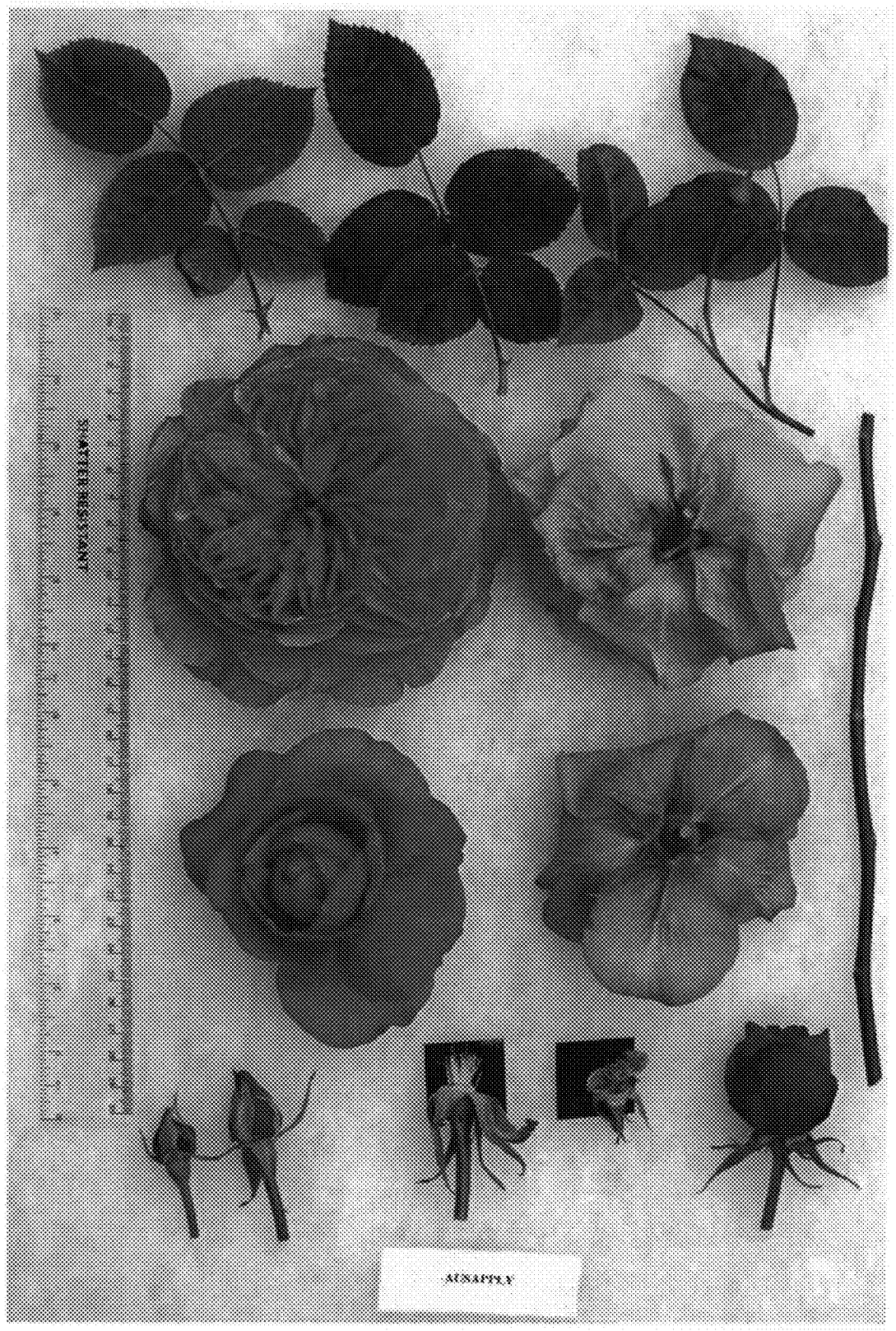
AUNAPTX.X